United States Patent
Brammer

(10) Patent No.: US 6,786,078 B2
(45) Date of Patent: Sep. 7, 2004

(54) VIBRATION PICKUP COMPRISING A CLAMPING SLEEVE

(75) Inventor: Hartmut Brammer, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/149,845

(22) PCT Filed: Dec. 14, 2000

(86) PCT No.: PCT/DE00/04471
§ 371 (c)(1),
(2), (4) Date: Oct. 17, 2002

(87) PCT Pub. No.: WO01/44772
PCT Pub. Date: Jun. 21, 2001

(65) Prior Publication Data
US 2004/0011135 A1 Jan. 22, 2004

(30) Foreign Application Priority Data
Dec. 15, 1999 (DE) .......................................... 199 60 328

(51) Int. Cl.⁷ ......................... G01L 23/22; G01P 15/09
(52) U.S. Cl. ..................................... 73/35.11; 73/654
(58) Field of Search ........................... 73/35.09–35.13, 73/654; 310/329

(56) References Cited
U.S. PATENT DOCUMENTS

| | | | | |
|---|---|---|---|---|
| 4,964,294 A | * | 10/1990 | Kawajiri et al. ........... 73/35.11 |
| 5,440,933 A | * | 8/1995 | Brammer et al. ............. 73/756 |
| 5,744,698 A | | 4/1998 | Genot |
| 5,872,307 A | * | 2/1999 | Brammer et al. .......... 73/35.11 |
| 5,939,616 A | * | 8/1999 | Ito et al. .................... 73/35.11 |
| 6,220,078 B1 | * | 4/2001 | Brammer et al. .......... 73/35.11 |
| 6,247,351 B1 | * | 6/2001 | Brammer et al. .......... 73/35.11 |

FOREIGN PATENT DOCUMENTS

| | | |
|---|---|---|
| DE | 44 03 660 | 10/1994 |
| DE | 195 24 147 | 1/1997 |
| DE | WO 99/01732 | * 1/1999 |
| DE | 197 27 703 | 1/1999 |

* cited by examiner

Primary Examiner—Hezron Williams
Assistant Examiner—John C. Hanley
(74) Attorney, Agent, or Firm—Kenyon & Kenyon

(57) ABSTRACT

A vibration sensor having a pressure sleeve in which the pressure sleeve may be mounted under pressure on a component causing vibration. To detect a vibration signal, e.g., in the case of a knock sensor, a sensory system is held by a seismic mass above it on the outside of the pressure sleeve via a screw connection on a contact face of the pressure sleeve under an axial prestress in the direction of the sensory system. The seismic mass has an inside thread and may be screwed onto the sensory system to produce the axial prestress in the direction of the sensory system. A seismic mass or the sensory system has at least two opposing grooves running radially opposite one another, so that the plastic may enter an interior space between the sensory system and the pressure sleeve during extrusion through these grooves.

8 Claims, 3 Drawing Sheets

VIBRATION PICKUP COMPRISING A CLAMPING SLEEVE

FIELD OF THE INVENTION

The present invention relates to a vibration sensor including a pressure sleeve.

BACKGROUND INFORMATION

German Published Patent Application No. 44 03 660 discusses a vibration sensor having a pressure sleeve which is used with knock sensors for monitoring the function of an internal combustion engine. This pressure sleeve is attached fixedly via a contact area to the component whose vibration is to be detected, in this case to the engine block of the combustion engine.

The vibration to be detected is the knocking sound of the engine during operation with this arrangement, the sound being transmitted via the pressure sleeve to a piezoceramic disk as the actual sensor element with contact disks and insulating disks in between them which permit signal pickup, thus generating an electric output signal suitable for analysis.

The type of mounting or clamping of this sensory system on the pressure sleeve and the mounting of the vibration sensor on the vibrating component have a great influence here on the method of manufacture as well as any false measurements and disturbances in operation. The clamping of the sensor element having a plurality of individual parts, e.g., with a spring and a seismic mass, is accomplished in this vibration sensor with a threaded ring, for example, which may be screwed onto a corresponding thread on the pressure sleeve.

In addition, a vibration sensor is also discussed in German Published Patent Application No. 195 24 147, in which the threaded ring and the spring in the form of a spring head nut are described as a one-piece component. This spring head nut may then be screwed onto the thread on the pressure sleeve and is thus in direct contact with the seismic mass.

SUMMARY OF THE INVENTION

A vibration sensor including a pressure sleeve in which the pressure sleeve is mountable under pressure with an initially concave base area on a component that is the source of vibrations may be provided in an exemplary embodiment of the present invention with a seismic mass with an internal thread that may be screwed onto the sensory system to produce the axial prestress.

In an exemplary embodiment of the present invention, it may be possible to mount a knock sensor on the engine block of an internal combustion engine inexpensively, because fewer individual parts may be needed and, in particular, a lower overall axial height and a lower weight of the vibration sensor may be feasible. Furthermore, omission of the plate spring, which may be present in the known arrangement, may also permit a more constant characteristic curve in detection of the sensor signal.

In a design of the vibration sensor having an injection-molded plastic housing around the pressure sleeve having a sensory system and the seismic mass, the seismic mass may have at least two grooves running radially opposite one another according to an exemplary embodiment of the present invention. Through these grooves the plastic may enter an interior space between the sensory system and the pressure sleeve during extrusion, thereby securing them, so this may permit a compact arrangement that may be mounted in any position, e.g., on the engine block.

In another exemplary embodiment having an injection-molded plastic housing, the sensory system may have at least two grooves running radially opposite one another. Through these grooves, the plastic may enter the interior space between the sensory system and the pressure sleeve during injection. Here again, any desired installation position may be possible, but it may be simpler and less expensive to manufacture a seismic mass without grooves. In both exemplary embodiments, the grooves may be provided on the two axial boundary surfaces of the seismic mass or the piezoceramic disk of the sensory system. They may be offset by 90° between one face and the other.

An especially good effect may be achieved in clamping the sensor element with the seismic mass if one or both axial boundary surfaces of the seismic mass are designed to be concave so that the axial wall thickness of the seismic mass may become smaller toward the center.

A vibration sensor in which a base area of the pressure sleeve may have a concave contour toward the inside radially before being mounted on a component may be designed so that the contact surface for the sensor element on the pressure sleeve may have a convex contour toward the inside radially before assembly. This contour may be designed so that after assembly, at least the sensory system may be largely in flat contact with the contact surface.

DETAILED DESCRIPTION

Figure 1:
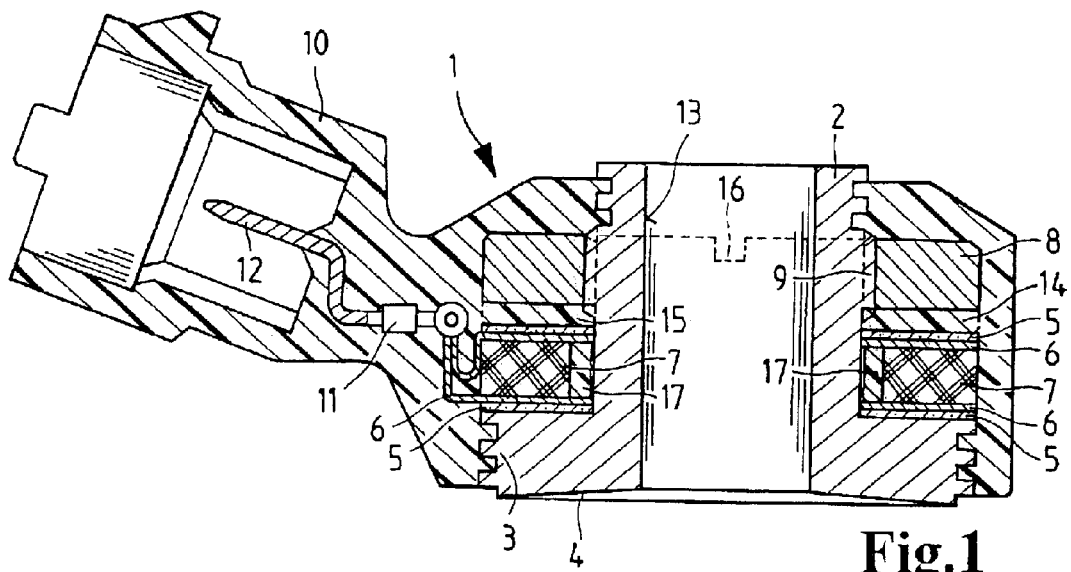
FIG. 1 shows a section through a knock sensor housing showing a vibration sensor including a pressure sleeve and a screw-on seismic mass having grooves.

FIG. 1 shows a vibration sensor in the form of a knock sensor for an internal combustion engine having an exterior plastic housing 1 in which a pressure sleeve 2 may be located. In the area of its lower end, pressure sleeve 2 may have a flange-like edge 3 by which it may be in contact at its lower bottom surface 4 with the engine block whose vibration is to be detected.

The following parts may be arranged on the outside circumference of pressure sleeve 2, starting from a lower contact face on flange-like edge 3: an insulating disk 5, a first contact disk 6, a piezoceramic disk 7 as the actual sensor element and above that a second contact disk 6 and a second insulating disk 5. A seismic mass 8 having an inside thread 9 may be placed on this arrangement and may be screwed onto pressure sleeve 2 in the direction of piezoceramic disk 7.

Electric terminals 11 for contact disks 6 and flat-pin plugs 12 may be injected in an integrated terminal part 10 of housing 1, which may be produced by a plastic extrusion method in particular. Flat-pin plugs 12 may thus be connected to the two contact disks 6, so there is an electric connection to the two sides of piezoceramic disk 7 via the two contact disks 6, and the electric voltage which may be generated by a pressure on piezoceramic disk 7 in the axial direction may be picked up.

A fastening screw may be passed through a central recess or a borehole 13 in pressure sleeve 2 for fastening this knock sensor as a whole to the engine block of the internal combustion engine either directly or indirectly. In mounting the known sensor, the entire torque which may be exerted by the fastening screw described above on pressure sleeve 2 may be transferred via bottom face 4, i.e., no force may act on piezoceramic disk 7 as the sensor element due to the mounting.

A prestressing force may act here, which may be generated by the pressure of screwed-on seismic mass 8. The prestressing force may be selected so that axial forces that may be at the limit of tolerability without any permanent deterioration of the electric signal may be acting on piezoceramic disk 7, and it may be largely independent of thermal expansion as well as compression of pressure sleeve 2 in mounting. The pulses which may be exerted by seismic mass 8 in proportion to the vibration of the engine may be converted to charge pulses which may be analyzed in a suitable device.

Figure 2:
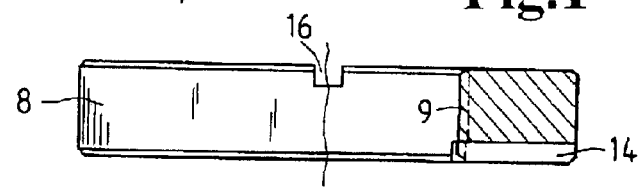
FIG. 2 shows a detail of the seismic mass according to FIG. 1.

In its lower area, seismic mass 8 may have grooves 14 and 15, which may also be clearly visible from the detail of seismic mass 8 according to FIG. 2. FIG. 2 also shows that in addition to grooves 14 and 15 radially opposite one another on one axial side of seismic mass 8, grooves 16 which may be offset by 90° may also be situated on the other axial side. During extrusion, through these grooves 14, 15 and 16 the plastic may enter an interior space 17 between piezoceramic disk 7 and pressure sleeve 2 to form housing 1.

Figure 3:
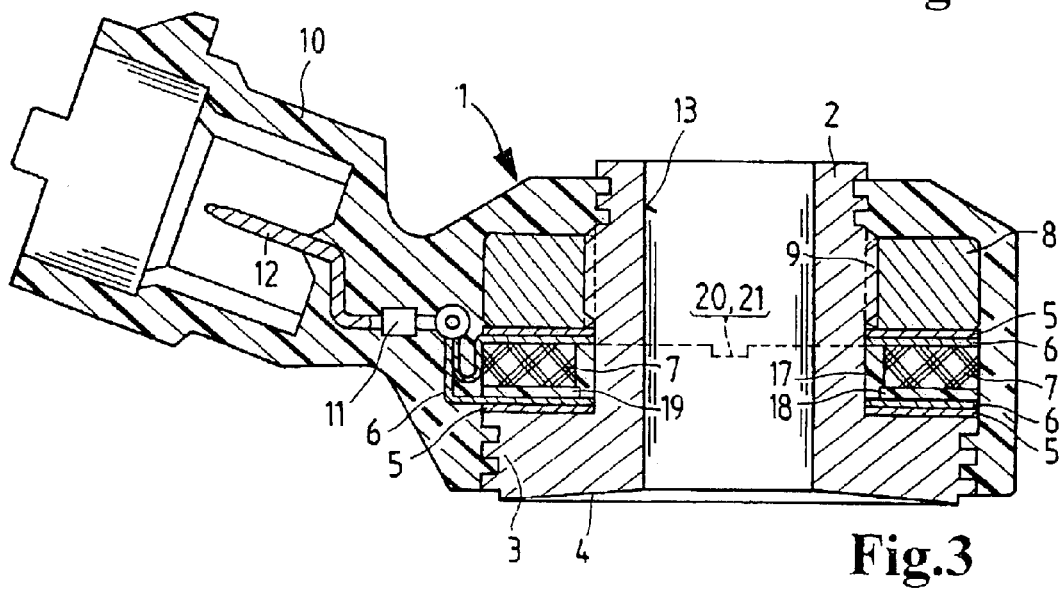
FIG. 3 shows a section through a knock sensor housing showing a vibration sensor including a pressure sleeve and a screw-on seismic mass plus a sensory system having grooves.
Figure 4:
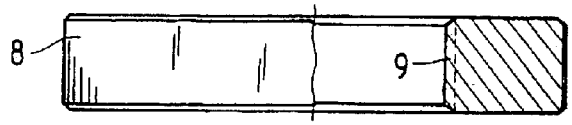
FIG. 4 shows a detail of the seismic mass according to FIG. 3.
Figure 5:
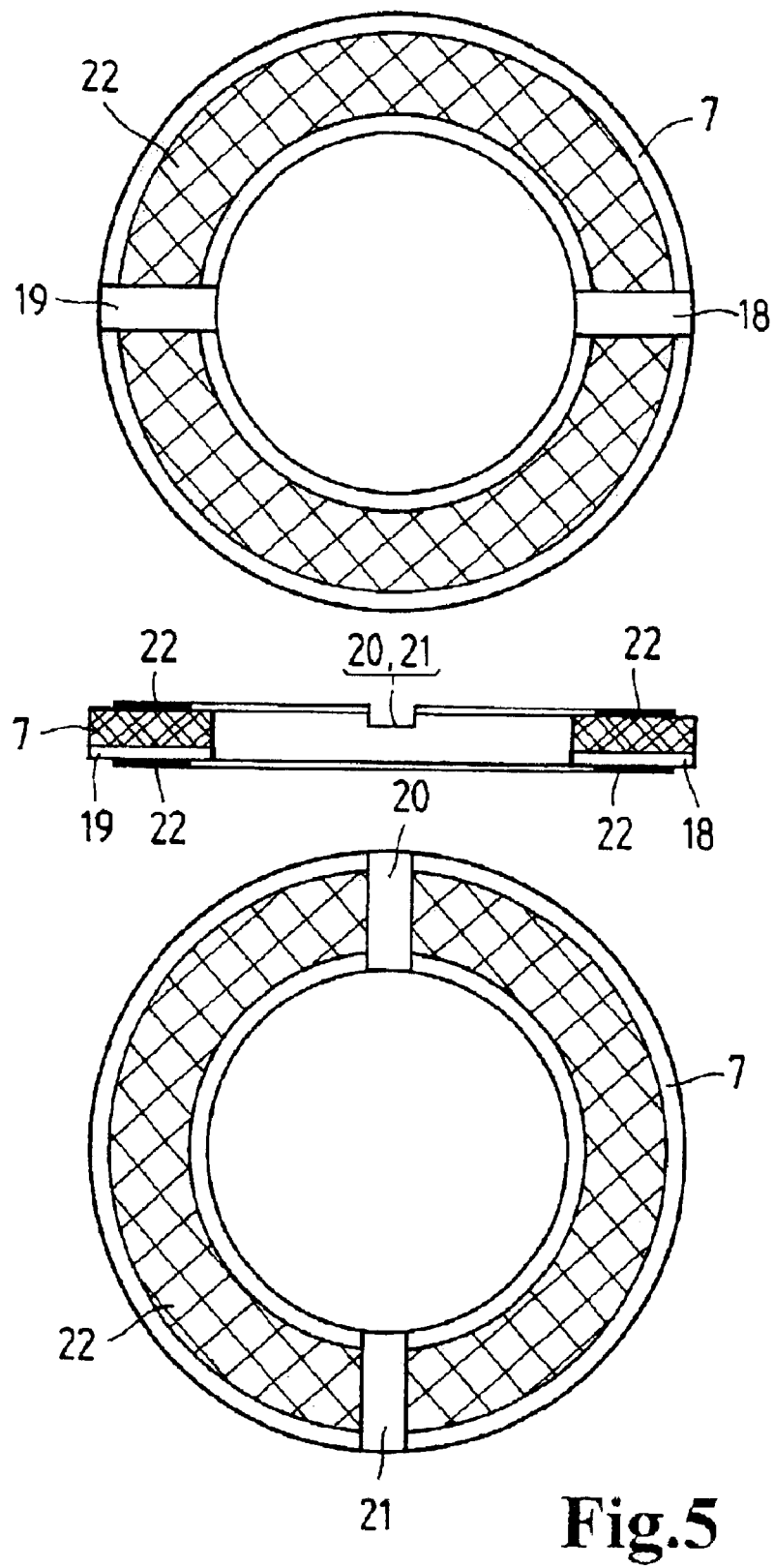
FIG. 5 shows a top view of the sensory system according to FIG. 3 having grooves.

In the exemplary embodiment according to FIGS. 3, 4 and 5, seismic mass 8 may be designed without grooves. The sensory system or piezoceramic disk 7 here may have grooves 18, 19 and 20, 21 which may be visible in the three views of piezoceramic disk according to FIG. 5. FIG. 5 may also show metallized surfaces 22, which may provide electric contacting of piezoceramic disk 7 on the two surfaces opposing one another axially via contact disks 6.

Figure 6:
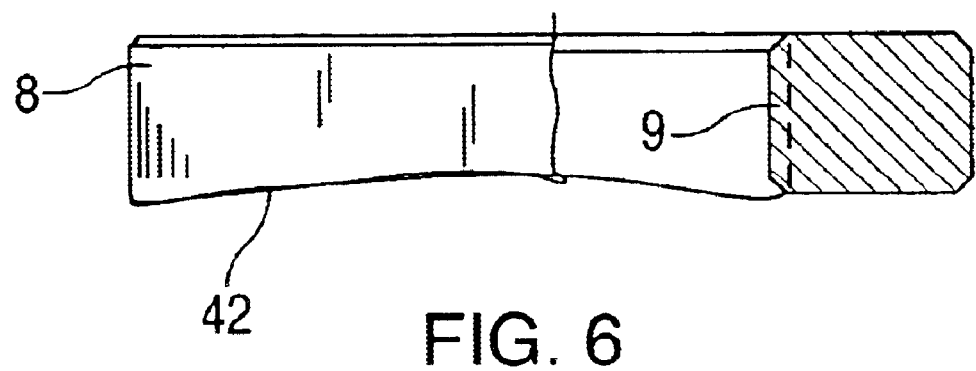
FIG. 6 is an example embodiment of a seismic mass.

As illustrated in FIG. 6, an especially good effect may be achieved in clamping the sensor element with the seismic mass 8 if one or both axial boundary surfaces of the seismic mass 8 are designed to be concave 42 so that the axial wall thickness of the seismic mass 8 may become smaller toward the center.

Figure 7:
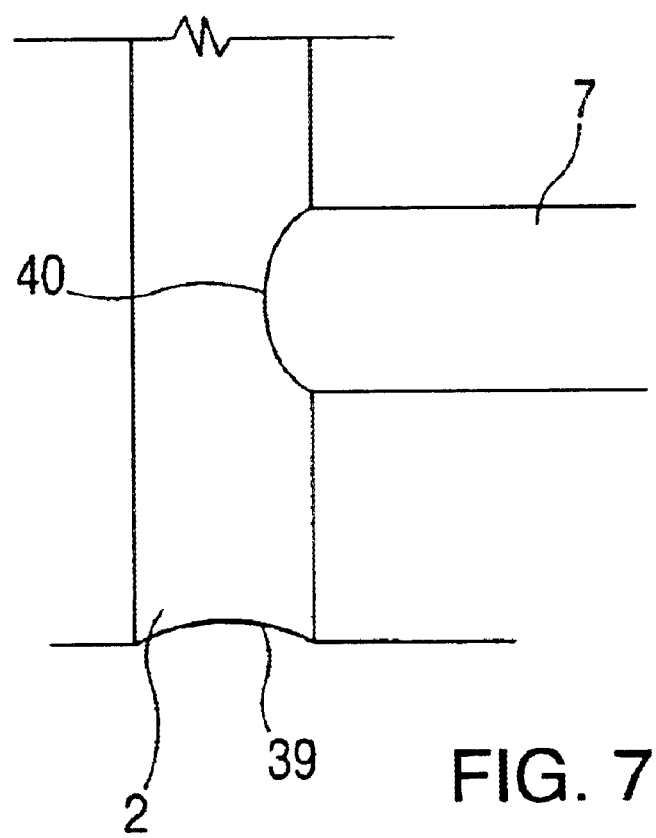
FIG. 7 is a cross sectional view of an example embodiment of a vibration sensor.

As illustrated in FIG. 7, a vibration sensor in which a base area 39 of the pressure sleeve 2 may have a concave contour toward the inside radially before being mounted on a component may be designed so that the contact surface for the sensor element 7 on the pressure sleeve 2 may have a convex contour 40 toward the inside radially before assembly. This contour 40 may be designed so that after assembly, at least the sensory system may be largely in flat contact with the contact surface.

What is claimed is:

1. A vibration sensor, comprising:
a pressure sleeve mountable under a mounting pressure on a component causing vibration;
a sensory system; and
a seismic mass located above the sensory system, the sensory system and the seismic mass being held together by a screw connection on an outside of the pressure sleeve on a contact face of a flange-like segment of the pressure sleeve under an axial prestress, wherein:
the seismic mass has an internal thread, the seismic mass able to be screwed on in a direction of the sensory system to produce the axial prestress in the direction of the sensory system, and
one of a plurality of axial boundary surfaces of the seismic mass is concave so that an axial wall thickness of the seismic mass becomes smaller towards a center of the seismic mass, wherein at least one of the seismic mass and the sensory system includes a plurality of grooves on at least one side, a plastic being introduceable through the plurality of grooves during an injection molding into an interior space between the sensory system and the pressure sleeve.

2. The vibration sensor according to claim 1, further comprising:
an injection-molded plastic housing formed around the pressure sleeve.

3. The vibration sensor according to claim 2, wherein the plurality of grooves include at least two radial, diametrically opposed grooves.

4. The vibration sensor according to claim 3, wherein the plurality of grooves are situated on both axial boundary surfaces, the plurality of grooves of the seismic mass offset 90° from each other.

5. The vibration sensor according to claim 2, wherein the plurality of grooves are situated on both axial boundary surfaces, the plurality of grooves of the seismic mass offset 90° from each other.

6. The vibration sensor according to claim 1, wherein:
a bottom surface of the pressure sleeve includes a first contour which runs radially inward in a concave manner prior to mounting the pressure sleeve on the component, the first contour changeable by the mounting pressure, and
the contact face includes a second contour which runs radially inward in a convex manner prior to mounting the pressure sleeve on the component, the second contour changeable by the mounting pressure, at least the sensory system lying about flat on the contact face after mounting.

7. A vibration sensor, comprising:
a pressure sleeve mountable under a mounting pressure on a component causing vibration;
a sensory system; and
a seismic mass located above the sensory system, the sensory system and the seismic mass being held together by a screw connection on an outside of the pressure sleeve on a contact face of a flange-like segment of the pressure sleeve under an axial prestress, wherein:
the seismic mass has an internal thread, the seismic mass able to be screwed on in a direction of the sensory system to produce the axial prestress in the direction of the sensory system, and
both axial boundary surfaces of the seismic mass are concave so that an axial wall thickness of the seismic mass becomes smaller towards a center of the seismic mass, wherein at least one of the seismic mass and the sensory system includes a plurality of grooves on at least one side, a plastic being introduceable through the plurality of grooves during an injection molding into an interior space between the sensory system and the pressure sleeve.

8. The vibration sensor according to claim 7, wherein the plurality of grooves are situated on both axial boundary surfaces, the plurality of grooves of the sensory system offset 90° from each other.

* * * * *